United States Patent [19]

Bittar

[11] Patent Number: 5,553,158
[45] Date of Patent: Sep. 3, 1996

[54] DEVICE FOR THE DATA PROCESSING OF LINEAR IMAGES OF GENERATRICES OF AN ARTICLE HAVING AN AXIS OF REVOLUTION

[75] Inventor: Bachar Bittar, Joinville, France

[73] Assignee: Est. Gilles Lerouz, France

[21] Appl. No.: 955,852

[22] PCT Filed: Apr. 23, 1992

[86] PCT No.: PCT/FR92/00367

§ 371 Date: Feb. 22, 1994

§ 102(e) Date: Feb. 22, 1994

[87] PCT Pub. No.: WO92/20034

PCT Pub. Date: Nov. 12, 1992

[30] Foreign Application Priority Data

Apr. 24, 1991 [FR] France .................................. 91 05364

[51] Int. Cl.⁶ ............................................ G06K 9/00
[52] U.S. Cl. ........................... 382/142; 382/141; 382/149
[58] Field of Search .............................. 382/8, 50, 51, 382/52, 142; 348/127; 250/223 B; 209/522, 535

[56] References Cited

U.S. PATENT DOCUMENTS

| | | | |
|---|---|---|---|
| 4,701,612 | 10/1987 | Strugill | 250/223 B |
| 4,941,191 | 7/1990 | Miller et al. | 382/54 |
| 4,958,223 | 9/1990 | Juvinall et al. | 382/8 |
| 5,034,990 | 7/1991 | Klees | 382/22 |
| 5,204,911 | 4/1993 | Schwatz et al. | 382/8 |
| 5,214,713 | 3/1993 | Juvinall | 382/8 |
| 5,305,391 | 4/1994 | Gomibuchi | 382/8 |
| 5,369,713 | 11/1994 | Schwartz et al. | 382/8 |
| 5,392,359 | 2/1995 | Futamura et al. | 382/8 |

*Primary Examiner*—Joseph Mancuso
*Assistant Examiner*—Bipin Shalwala
*Attorney, Agent, or Firm*—Ostrolenk, Faber, Gerb & Soffen L.L.P.

[57] ABSTRACT

The present invention relates to a device for the data processing of linear images of generatrices of an article having an axis of revolution.

The images being detected by a linear image detector having photosensitive points, the device has a memory (24) and a calculator (23) adapted to calculate, for each point of the linear image detector, data values of images coming from such point during a first processing period which corresponds to a complete revolution of the article and to store said average value in the memory (24).

The device also has a memory (21) adapted to store all the image data coming from the linear image detector during the course of a complete revolution of the article and restore them during a second processing period after the first processing period.

Finally, it comprises a threshold memory (26) which, for each point of the photosensitive detector, stores at least the threshold information.

The invention applies to the inspection of bodies of revolution.

5 Claims, 2 Drawing Sheets

DEVICE FOR THE DATA PROCESSING OF LINEAR IMAGES OF GENERATRICES OF AN ARTICLE HAVING AN AXIS OF REVOLUTION

BACKGROUND OF THE INVENTION

1. Field of the Invention

The present invention relates to a data processing device for images of an article having an axis of rotation, applicable in particular to the inspection of machined parts, food cans and beer cans.

2. Description of the Related Art

Devices for inspection of articles of revolution known up to the present time generally have a linear camera which receives an image of a generatrix of the revolving article and thresholds, generally two in number, common to all the photosensitive points of the linear camera. If the thresholds are exceeded an error signal is output.

These devices therefore require an initial calibration for each series of identical articles treated and a recalibration upon every change in series. Furthermore, the light illuminating the article must be of uniform intensity and isotropic. Otherwise, the reflections of light off of the articles cause detections of defects and produce an erroneous inspection result.

For these various reasons, the devices known at the present time are limited to a rough inspection which tolerates the less noticeable defects of relatively cylindrical articles which do not have convergent reflections.

The amount of image data to be treated during an inspection excludes the use of data processing software which uses all of the image data.

SUMMARY OF THE INVENTION

The present invention is directed at overcoming these drawbacks by providing a device which stores, for each photosensitive point of the image detector, the average of the brightnesses observed during a complete revolution of the article inspected and applies thresholds as a function of this average.

In this way, reflections are compensated for and calibration of the device is not necessary.

The object of the present invention is thus a data device for processing the data of linear images of generatrices of an article having an axis of revolution, the images being detected by a linear image detector having photosensitive points and the device being characterized by the fact that it has a memory and a calculator, the calculator being adapted to calculate, for each point of the linear image detector, data values of images coming from the point during a complete revolution of the article and to store the average value in the memory.

The description which follows, read with reference to the accompanying drawing and given by way of illustration and not of limitation, will make it possible better to understand the advantages, purposes and characteristics of the present invention.

DETAILED DESCRIPTION OF A PREFERRED EMBODIMENT

Figure 1:
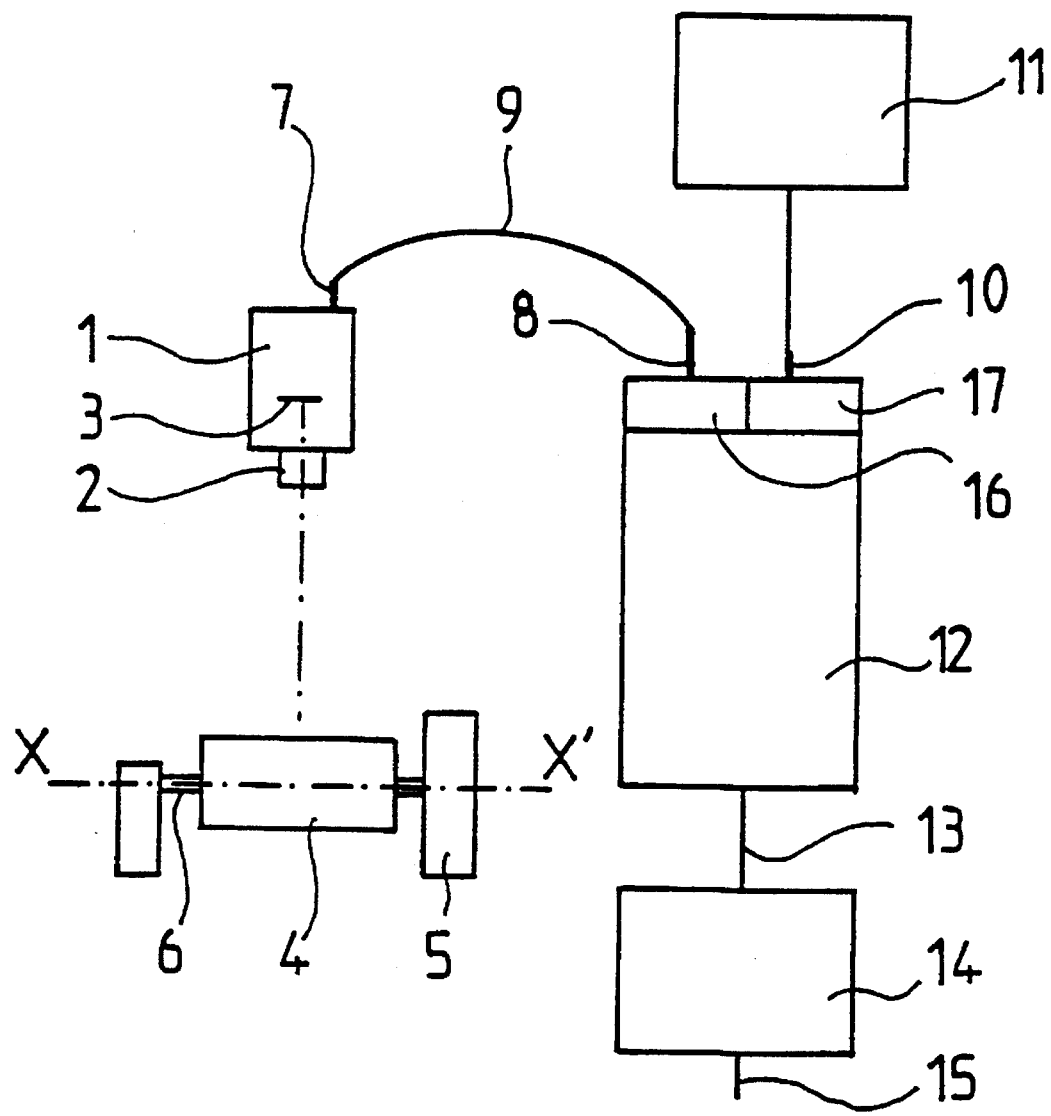
FIG. 1 is a schematic view of a system for the inspection of bodies of revolution which incorporates the device in accordance with the invention.

Referring to FIG. 1, a linear camera 1 having a linear image detector 3 and a lens 2 is provided for forming an image of a generatrix of an article of revolution 4 on the image detector 3. The article 4, which has an axis of revolution XX', is rotatably supported by a drive shaft 6 and rotated by a motor 5. An electronic signal connector 7 is connected, via an electric cable 9, to a signal input 8 of an analog-digital converter 16 which is electrically connected to an image data processing card 12. The image data processing card 12 is connected, by an electric cable 13, to a computer 14 having connectors 15 and to a display card 17, which is connected by a connector 10 to a monitor 11.

The linear camera 1 is electronic thereby providing through the connector 7, electronic signals representative of the image received by the image detector 3, which is linear and has photosensitive points. The lens 2 is of a known type. The image detector 3 is parallel to the axis of revolution XX' of the article 4. The motor 5 and the drive shaft 6 are of known types. The other elements are of known type, with the exception of the image data processing card 12, which is shown in FIG. 2.

The image data processing card 12 has the function of detecting defects in the article 4 by processing the data received from the analog-digital converter 16. These defects, as well as, the images detected, can be displayed on the monitor 11. The computer 14 is adapted to process the data coming from the card 12 and to estimate the quality of the article 4.

Figure 2:
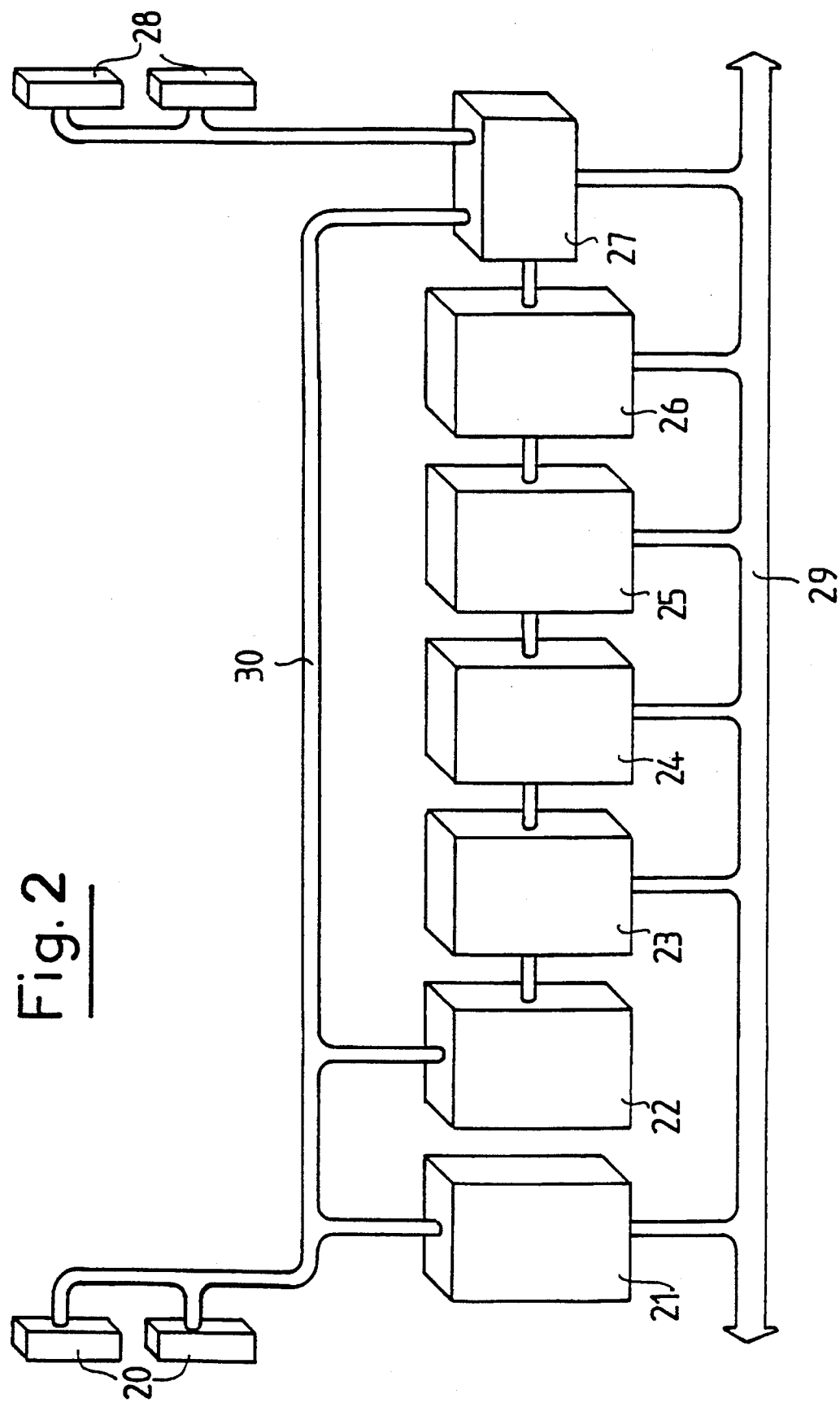
FIG. 2 shows an electronic diagram of the device according to the invention.

In FIG. 2, one embodiment of the image data processing card 12 is shown. FIG. 2 shows an image data input connector 20 connected to an image bus 30, an image memory 21 connected to the image bus 30, a buffer memory 22 also connected to the image bus 30, an average calculator 23 connected to the buffer memory 22, an average and severity memory 24 connected to the average calculator 23, a threshold calculator 25 connected to the memory 24, a threshold clearance calculator 26 connected to the threshold calculator 25, a threshold clearance buffer memory 27 connected to the threshold clearance calculator 26 and to the image bus 30, an image data output connector 28 connected to the buffer memory 27 and a system bus 29, connected to the articles 21 and 23 through 27.

The image data input connector 12 connects the analog-digital converter 16, shown in FIG. 1, to the card 12. The image bus 30, accordingly, permits the transfer of digital data representative of the luminous intensities detected by the photosensitive points of the linear image detector 3. The image memory 21 is adapted to store all the image data passing over the image bus 30 during a complete revolution of the article 1, thus referred to as the primary processing period, and restoring all the image data on the image bus 30 during a second processing period. The buffer memory 22 is of the summation memory type, also known as a storage memory. For each point of the linear detector 3, it stores the sum of the digital values passing over the image bus 30 and corresponding to that point during the first processing period. The buffer memory 22 also effects the summation of the images obtained during the first processing period. For each point of the linear image detector 3, the average calculator 23 divides the sum stored in the buffer memory 22 by the number of pictures taken by the image detector 3 during the first processing period.

The average calculator 23 is preferably formed of a conversion table, generally referred to as a "look-up table", the transfer function of which is given by the computer 14.

The average and severity memory 24 is adapted to store the averages calculated by the average calculator 23. Furthermore, the computer 14 loads into this memory 24, for each point of the image detector 3, the number of a severity table selected from among several tables, each containing severity rates. These severity rates are preferably expressed in percentage variation from the average value and correspond to zones of the image detector 3 which can be parametered in length.

The threshold calculator 25 calculates, as a function of the average and severity data contained in the memory 24, the digital values of the value thresholds of the signals passing over the image bus 30. These thresholds, which may be numerous for each point of the image detector 3, are the products for each point of the average of the luminous intensities detected by the respective point and the rates of severity. The threshold calculator is preferably formed by as many look-up tables as the maximum number of thresholds selected.

The threshold memory 26 is adapted to restore these threshold values. This memory 26 is preferably of the look-up table type, and the thresholds calculated are stored as a transfer function, the values present between two thresholds being transformed, at the output, into threshold clearance signals.

The threshold clearance buffer memory 27 has two functions. The first function of the buffer memory 27 is to compare, in succession for all points of the image detector 3, the value of the digital signal passing over the image bus 30 with the thresholds supplied by the threshold memory 26. The second function of the buffer memory 27 is to store only the numbers of points of the image detector 3 which correspond to a change, in threshold clearances as compared with the preceding point of said detector 3, associating with these numbers of points, called transition points, the direction of threshold clearance and the threshold number reached after this transition.

The buffer memory 27 therefore operates during the second period.

The values stored in the buffer memory 27 are subsequently transferred to the computer 14 for processing.

For example, if the maximum number of thresholds attributed is four, the threshold calculator 25 has four look-up tables. If the computer 14 gives the severity rates 30% 60% 150% and 200% for the point 1, it then loads a severity table which is numbered 1 and assigns the severity table number 1 to the point 1. The severity table numbered 1 corresponds to four look-up tables which, in succession, effect the multiplication of the number arriving at their input by the coefficients 0.3, 0.6, 1.5 and 2. The threshold memory 26 then has four memories addressed in parallel, each of which retains, for the point 1, one of the products of the average given, for this point, by the average memory 24 and one of the coefficients 0.3, 0.6, 1.5 or 2. The threshold clearance buffer memory 27 has four comparators which compare these products with the digital value of the signal corresponding to this point and outputs four signals indicating whether the digital value is greater than or less than each of these thresholds. The transitions corresponding to a change in these signals between two successive points of the image detector are stored in the buffer memory with the direction of transition from one threshold to the other and the threshold reached after this transition. In this way, the only data stored in the buffer memory 27 are, for each line, the numbers of the points corresponding to these transitions, the transition directions, and the numbers of thresholds reached after these transitions. These data correspond to contours.

The first processing period corresponds to the complete revolution of the article 4, the second period corresponds to the restitution by the image memory 21 of the image data which it retains.

In accordance with a variant, the second period corresponds to a new complete revolution of the article 4 and to a new series of pictures by the image detector 3.

The system bus 29, connected to the computer 14, permits access to the various memories and look-up tables, as well as, to the control of the operating sequences of the electronic components of the card 12 which are indicated in FIG. 2.

The operation of the electronic card shown in FIG. 2 is simple. It permits the output, synchronously with the data retrieved from the memory 21, of the clearance signals which correspond to defects in the article or to regions of marking or writing.

The computer 14 is then adapted to process these data in order to estimate the quality of the article 4, or in order to read the writings or symbols which it bears and sort the articles 4 accordingly.

One of the advantages of the device forming the object of the present invention as shown in FIG. 2 is that it permits the processing in masked time of the article 4 inspected during the second processing period, since the processing is then effected on images stored in the memory 21.

It should be noted that the device forming the object of the present invention permits the processing of contours and surfaces, the processing of contours coming from the buffer memory 27 and the processing of surfaces coming from the comparators incorporated in the buffer memory 27.

I claim:

1. A data processing device for processing linear images of generatrices of an article having an axis of revolution, the linear images being detected by a linear image detector having photosensitive points for detecting linear images and for outputting image data representing linear images detected by the linear image detector, the device comprising:

a calculator for calculating for each point of the linear image detector an average value of the image data output from a respective photosensitive point of the linear image detector during a first period of processing, the first period corresponding to a complete revolution of the article;

an average memory for storing the average value for each point of the linear image detector;

a severity memory for storing a plurality of severity tables containing a plurality of severity coefficients and for storing for each photosensitive point of the image detector a severity table number selected for a respective photosensitive point and n number of severity coefficients contained in one of said plurality of severity tables corresponding to the severity table number, where n is an integral number equal to or greater than one, the severity coefficients being expressed in a percentage of variation from the average value stored in the average value memory; and a threshold calculator for calculating n number of thresholds for each photosensitive point of the linear image detector by multiplying the average value for a respective photosensitive point by each of the n number of severity coefficients for the respective photosensitive point.

2. The device of claim 1, wherein n is an integer equal to or greater than two.

3. The device of claim 1, further comprising:

a threshold memory for storing n number of thresholds for each photosensitive point of the linear image detector, the threshold memory being formed of a look-up table having a transfer function which causes each of the n threshold values to correspond to each average value; and a threshold clearance buffer memory having n number of comparators for comparing an image signal output from each of the photosensitive points with each of the n thresholds assigned to each respective photosensitive point and for outputting n status signals for indicating whether said image signal is greater than or less than each of the n thresholds, said comparator performing the comparing during a second processing period occurring after the first processing period and during which the article rotates a second complete revolution.

4. The device of claim 3, wherein the threshold clearance buffer memory stores only the data corresponding to the points which, as compared with the preceding point of the image detector, do not correspond to the same threshold clearance data.

5. The device of claim 3, further comprising a computer for loading the severity table numbers into the severity memory, for initializing the values stored in the average memory, the threshold memory and the threshold clearance buffer memory and for processing the threshold clearance data.

* * * * *